United States Patent [19]

Kogan et al.

[11] Patent Number: 5,510,332
[45] Date of Patent: Apr. 23, 1996

[54] PROCESS TO INHIBIT BINDING OF THE INTEGRIN $\alpha_4\beta_1$ TO VCAM-1 OR FIBRONECTIN AND LINEAR PEPTIDES THEREFOR

[75] Inventors: Timothy P. Kogan; Kaijun Ren, both of Sugar Land; Peter Vanderslice; Pamela J. Beck, both of Houston, all of Tex.

[73] Assignee: Texas Biotechnology Corporation, Houston, Tex.

[21] Appl. No.: 271,830

[22] Filed: Jul. 7, 1994

[51] Int. Cl.$^6$ .............................. A61K 38/00; C07K 1/00
[52] U.S. Cl. .................. 514/14; 514/15; 514/16; 514/17; 514/18; 530/327; 530/328; 530/329; 530/330; 530/345
[58] Field of Search .................. 530/327–330, 530/345; 514/14–18

[56] References Cited

U.S. PATENT DOCUMENTS 5,405,831   4/1995   MacIntyre ................................ 514/4

OTHER PUBLICATIONS

The Journal of Cell Biology, *Activation–dependent Recognition by Hematopoietic Cells of the LDV Sequence in the V Region of Fibronectin;* E. A. Wayner and N. L. Kovach, vol. 116, No. 2, 489–497 (Jan. 1992).
Cell, *Phosphatidylinositol 3–Kinase: Structure and Expression of the 110 kd Catalytic Subunit*, Hiles et al., vol. 70, 419–429 (Aug. 7, 1992).
Journal of Cell Science, *VCAM–1 is a CS1 peptide–inhibitable adhesion molecule expressed by lymph node high endothelium*, May et al., vol. 106, 109–119 (1993).
American Journal of Pathology, *Rapid Communication–Alternative Splicing of Human VCAM–1 in Activated Vascular Endothelium*, Cybulski et al., vol. 138, No. 4, 815–820, (Apr. 1991).
The Journal of Biological Chemistry, *Competitive Binding of Vascular Cell Adhesion Molecule–1 and the HepII/IIICS Domain of Fibronectin to the Integrin $\alpha_4\beta_1$*, Makarem et al., vol. 269, No. 6, 4005–4011 (Feb. 1994).
Cell, *VCAM–1 on Activated Endothelium Interacts with the Leukocyte Integrin VLA–4 at a Site Distinct from the VLA–4/ Fibronectin Binding Site*, Elices et al. vol. 60, 577–584, (1990).
Cell, *Direct Expression Cloning of Vascular Cell Adhesion Molecule 1, a Cytokine–Induced Endothelial Protein That Binds to Lymphocytes*, Osborn et al., vol. 9, 1203–1211, (1989).
Science, *An Inducible Endothelial Cell Surface Glycoprotein Mediates Melanoma Adhesion*, G. Edgar Rice and Michael P. Bevilacqua, vol. 246, 1303–1306 (Dec. 1989).
The Journal of Biological Chemistry, *Cloning of an Alternate Form of Vascular Cell Adhesion Molecule–1 (VCAM1)*, Hession et al., vol. 266, Issue No. 11, 6682–6685 (1991).

J. Exp. Med., *Lymphocyte Adhesion through Very Late Antigen 4: Evidence for a Novel Binding Site in thew Alternatively Spliced Domain of Vascular Cell Adhesion Molecule 1 and an Additional $\alpha 4$ Integrin Counter–Receptor on Stimulated Endothelium*, Robert H. Vonderheide and Timothy A. Springer, vol. 175, 1433–1442 (Jun. 1992).
J. Exp. Med., *Activated Endothelium Binds Lymphocytes Through a Novel Binding Site in the Alternatively Spliced Domain of Vascular Cell Adhesion Molecule–1*, Laurelee Osborn and Christopher D. Benjamin, vol. 176, 99–107 (Jul. 1992).
The Journal of Biological Chemistry, *VLA–4 Integrin Mediates Lymphocyte Migration of the Inducible Endothelial Cell Ligand VMCA–1 and the Extracellular Matrix Ligand Fibronectin*, Po–Ying Chan and Alejandro Aruffo, vol. 268, No. 33, 24655–24664 (Nov. 24, 1993).
The EMBO Journal, *Identification of a novel recognition sequence for the integrin $\alpha 4\beta 1$ in the COOH–terminal heparin–binding domain of fibronectin*, A. Paul Mould and Martin J. Humphries, vol. 10, No. 13, 4089–4095 (1991).
J. Clin Invest. *VLA–4 Integrin Can Mediate CD11/ CD18–independent Transendothelial Migration of Human Monocytes*, H. Eduardo Chuluyan and Andrew C. Issekutz, vol. 92, 2768–2777 (Dec. 1993).
Nature, *Prevention of experimental autoimmun e encephalomyelitis by antibodies against $\alpha 4\beta 1$ integrin*, Yednock et al., vol. 356, 63–66 (5 Mar. 1992).
Eur J. Immunol, *Monoclonal antibodies to the integrin $\alpha$–4 subunit inhibit the murine contact hypersensitivity response*, Chisholm et al., vol. 23, 682–688 (1993).
The Journal of Biological Chemistry, *Multiple Activation States of VLA–4*, Akihide Masumoto and Martin E. Hemler, vol. 268, No. 1, 228–234 (Jan. 5, 1993).
1994 Current Drugs Ltd., Abstract of Publication No. WO9402445, *Non–peptidic surrogates of the LDV sequence and their use in the treatment of inflammation, autoimmune diseases and tumour progression*, Lider et al.
The Journal of Biological Chemistry, *The CS5 Peptide Is a Second Site in the IIICS Region of Fibronectin Recognized by the Integrin $\alpha_4\beta_1$*, Mould et al., vol. 266, No. 6, 3579–3585 (Feb. 25, 1991).

*Primary Examiner*—Christina Y. Chan
*Assistant Examiner*—Benet Prickril
*Attorney, Agent, or Firm*—Dressler, Goldsmith, Shore & Milnamow, Ltd.

[57] ABSTRACT

The present invention is directed to an isolated and purified peptide comprising the LDV domain of the CSI peptide sequence or single amino acid substitutent analog thereof. A preferred peptide has the amino acid residue sequences shown in SEQ ID NOs:8–14, 17–23, 25, 28, and 51. The present invention is further directed to a process of inhibiting the binding of $\alpha_4\beta_1$ integrin to a protein such as VCAM-1 or fibronectin comprising exposing a cell that expresses $\alpha_4\beta_1$ integrin to the protein in the presence of an effective inhibiting amount of such a peptide. The present invention is still further directed to a pharmaceutical composition comprising a peptide of SEQ ID NO:8–102.

15 Claims, No Drawings

PROCESS TO INHIBIT BINDING OF THE INTEGRIN α₄β₁ TO VCAM-1 OR FIBRONECTIN AND LINEAR PEPTIDES THEREFOR

FIELD OF THE INVENTION

This invention relates generally to a process for inhibiting the binding of $\alpha_4\beta_1$ integrin to proteins such as VCAM-1 and fibronectin. The invention also relates to synthetic linear peptides that inhibit that binding.

BACKGROUND OF THE INVENTION

Vascular cell adhesion molecule-1 (VCAM-1) is a protein that is found on the surface of endothelial cells that line the interior wall of capillaries. VCAM-1 recognizes and binds to the integrin $\alpha_4\beta_1$ (or VLA-4 for very late antigen-4), a heterodimeric protein present on the surface of certain white blood cells. Binding of $\alpha_4\beta_1$ to VCAM-1 allows white blood cells to adhere to the capillary wall in areas where the tissue surrounding the capillary has been infected or damaged.

When a tissue has been invaded by a microorganism or has been damaged, white blood cells, also called leukocytes, play a major role in the inflammatory response. One of the most important aspects of the inflammatory response involves the cell adhesion event. Generally, white blood cells are found circulating through the bloodstream. However, when a tissue is infected or becomes damaged, the white blood cells recognize the invaded or damaged tissue, bind to the wall of the capillary near the affected tissue and diffuse through the capillary into the affected tissue. VCAM-1 helps certain types of white blood cells recognize the affected sites, bind to the capillary wall, and migrate into the affected tissue.

There are three main types of white blood cells: granulocytes, monocytes and lymphocytes. VCAM-1 binds to $\alpha_4\beta_1$ expressed on the surface of monocytes, lymphocytes and two subclasses of granulocytes-eosinophils and basophils.

Monocytes, after leaving the bloodstream through the wall of a capillary, mature into macrophages that phagocytose and digest invading microorganisms, foreign bodies and senescent cells. Lymphocytes produce antibodies and kill infected cells. Eosinophils and basophils secrete mediators of various inflammatory reactions.

Following infection or damage of tissue surrounding a capillary, the endothelial cells that line the capillary express a series of adhesion molecules, including VCAM-1, that are critical for binding white blood cells that are necessary for fighting infection. Prior to binding to VCAM-1, the white blood cells initially bind to another set of adhesion molecules to slow their flow and allow the cells to "roll" along the activated endothelium. Monocytes, lymphocytes, basophils and eosinophils are then able to firmly bind to VCAM-1 on the endothelial cells via the a $\alpha_4\beta_1$ integrin. There is evidence that this interaction is also involved in transmigration of these white blood cells into the damaged tissue.

Although white blood cell migration to the site of injury helps fight infection and destroy foreign material, in many instances this migration can become uncontrolled, with white blood cells flooding to the scene, causing widespread tissue damage. Compounds capable of blocking this process, therefore, may be beneficial as therapeutic agents. Thus, it would be useful to develop inhibitors that would prevent the binding of white blood cells to VCAM-1.

For example, some of the diseases that might be treated by the inhibition of $\alpha_4\beta_1$ binding include, but are not limited to, atherosclerosis, rheumatoid arthritis, asthma, allergy, multiple sclerosis and type I diabetes. In addition to being found on some white blood cells, $\alpha_4\beta_1$ is found on various cancer cells, including leukemia, melanoma, lymphoma and sarcoma cells. It has been suggested that cell adhesion involving $\alpha_4\beta_1$ may be involved in the metastasis of certain cancers. Inhibitors of $\alpha_4\beta_1$ binding may, therefore, also be useful in the treatment of some forms of cancer.

BRIEF SUMMARY OF THE INVENTION

In one aspect, the present invention provides an isolated and purified linear peptide of from 4 to about 13 amino acid residues having (a) an N-terminal amine group, acetyl group or a polyethyleneglycol moiety of from about 400 to about 12,000 Daltons avemge molecular weight linked through an amide bond to the N-terminal residue; and (b) a C-terminal carboxylic acid group or amide group; the peptide comprising the amino acid residue sequence Trp-Leu-Asp-Val (SEQ ID NO:1) or a single amino acid substituent analog thereof. The single substituent analog has the amino acid residue sequence Trp-Xaa₁-Asp-Val (SEQ ID NO:2) or Trp-Leu-Asp-Xaa₂ (SEQ ID NO:3), where Xaa and Xaa₂ are any L-α-amino acid.

In a preferred embodiment, Xaa t is Ala, Cys, Gly, His, Lys, Leu, Met, Asn, Pro, Thr, Trp or Tyr and Xaa₂ is Ala, Cys, Phe, Gly, His, Ile, Leu, Gln, Arg, Ser, Thr, Vat, Trp or Tyr. More preferably, Xaa is Leu, Lys or Met and Xaa₂ is Vat, Tyr, Trp or Phe.

In yet another embodiment, a peptide of the present invention comprises the amino acid residue sequence Glu-Trp-Leu-Asp-Val (SEQ ID NO:4) or a single amino acid substituent analog thereof. Such an analog has the amino acid residue sequence of Xaa₃-Trp-Leu-Asp-Val (SEQ ID NO:5), Glu-Trp-Xaa₁-Asp-Val (SEQ ID NO:6), or Glu-Trp-Leu-Asp-Xaa₂ (SEQ ID NO:7), where Xaa₁ and Xaa₂ are as defined in SEQ ID NO: 1 and Xaa₃ is any D- or L-α-amino acid. Preferred embodiments of Xaa₁₋₂ are the same as set forth above. Preferably, Xaa₃ is Glu, Asn, Pro, Gln, Ser, Thr, Tyr or Val. In a particular embodiment, the Val residue of SEQ ID NOs:4–7 can be removed and still obtain a peptide of the present invention that inhibits $\alpha_4\beta_1$ binding.

In a preferred embodiment, a peptide of the present invention has the amino acid residue sequence of any of SEQ ID NOs:8–102 and, more preferably the sequence of SEQ ID NO:8–14, 17–23, 25, 28, and 51.

In another aspect, the present invention provides a pharmaceutical composition comprising a physiologically acceptable diluent and a peptide of the present invention.

In yet another aspect, the present invention provides a process of inhibiting the binding of $\alpha_4\beta_1$ integrin to VCAM-1. That process comprises exposing a cell expressing the $\alpha_4\beta_1$ integrin to a cell expressing VCAM-1 in the presence of an effective inhibiting amount of a peptide of the present invention. Preferably, a peptide used in that process has the amino acid residue sequence of SEQ ID NO:8–102 and, more preferably the amino acid residue sequence of SEQ ID NO:8–14, 17–23, 25, 28, and 51. In a preferred embodiment of that process, the VCAM 1 is on the surface of a vascular endothelial cell. In another preferred embodiment, the $\alpha_4\beta_1$ integrin is on the surface of a white blood cell such as a monocyte, a lymphocyte, a granulocyte (an eosinophil or a basophil) a stem cell or other cell naturally expressing $\alpha_4\beta_1$. Preferred peptides used in that process are the same as set forth above.

Where the cells are located in a living organism, a peptide is preferably administered to the organism in an effective inhibiting amount in a pharmaceutical composition of this invention.

In another aspect, the present invention provides a process of selectively inhibiting the binding of $\alpha_4\beta_1$ integrin to a protein comprising exposing the integrin to the protein in the presence of an effective inhibiting amount of a cyclic peptide of the present invention. Preferably, the $\alpha_4\beta_1$ integrin is expressed on the surface of a cell such as a white blood cell or stem cell and the protein is part of the extracellular matrix such as fibronectin.

DETAILED DESCRIPTION OF THE INVENTION

I. The Invention

The present invention provides a process of inhibiting the binding of $\alpha_4\beta_1$ integrin to proteins such as VCAM-1, fibronectin and invasin. The invention also provides peptides that inhibit that binding.

The adhesion of leukocytes to the vascular endothelium and their subsequent extravasation into tissues are critical steps in the inflammatory response (Springer, 1990). Vascular cell adhesion molecule-1 (VCAM-1), a member of the immunoglobulin superfamily, is expressed by endothelial cells and a restricted number of other cell types. VCAM-1 can be induced by endothelium cytokines such as tumor necrosis factor-$\alpha_1$, interleukin-4, and interleukin-1$\beta$ and is therefore hypothesized to contribute to leukocyte extravasion in inflammatory conditions such as rheumatoid arthritis, asthma, and atherosclerosis.

One molecular form of VCAM-1 contains seven immunoglobulin modules in its extracellular domain. VCAM-1 is recognized by the integrin receptor $\alpha_4\beta_1$. $\alpha_4\beta_1$ is expressed principally by leukocytes (T and B lymphocytes, monocytes, basophils, and eosinophils), and is also functional on mast cells, derivatives of the embryonic neural crest and in developing muscle.

$\alpha_4\beta_1$ also recognizes the extracellular matrix glycoprotein fibronectin. Three distinct $\alpha_4\beta_1$-binding sites have been identified within fibronectin, and all have been reproduced in synthetic form. One site (represented by the peptide H1) is found in the HepII region and is therefore expressed in all fibronectin isoforms; two others (represented by peptide CS1 and CS5) are present in the alternatively spliced type III connecting segments. Of these three, the CS1 peptide has the higher affinity for $\alpha_4\beta_1$ (Mould and Humphries, 1991) and contains the tripeptide Leu-Asp-Val (LDV) as its minimal active site. H1 contains a related motif, Ile-Asp-Ala (IDA), while CS5 incorporates a variant of the prototypic RGD motif, Arg-Glu-Asp-Val.

II. Peptides

In one aspect, the present invention provides peptides that inhibit binding of the $\alpha_4\beta_1$ integrin to proteins such as VCAM-1, fibronectin and invasin. A peptide of the present invention is modeled after a portion of the CS1 peptide that includes the LDV domain of the CSI peptide presented in such a way by its novel flanking sequence to produce a potent inhibitor of $\alpha_4\beta_1$ binding.

Peptides are disclosed herein as amino acid residue sequences. Those sequences are written left to right in the direction from the amino (N) to the carboxyl (C) terminus. Amino acid residue sequences are denominated by either a single letter or a three letter code. The meanings of those codes as well as various other abbreviations used herein are in accordance with the recommendation of the IUPAC-IUB Joint Commission on Biochemical Nomenclature, and are shown below.

| | | |
|---|---|---|
| A | Ala | L-alanine |
| Ac | | acetyl |
| Aic | | 2-aminoindan-2-carboxylic acid |
| Acm | | acetamidomethyl |
| C | Cys | L-cysteine |
| dC | dCys | D-cysteine |
| C(SO$_3$H) | | L-cysteic acid |
| tBu | | tert-butyl |
| D | Asp | L-aspartic acid |
| dD | dAsp | D-aspartic acid |
| E | Glu | L-glutamic acid |
| dE | dGlu | D-glutamic acid |
| <E | | L-pyroglutamic acid |
| F | Phe | L-phenylalanine |
| G | Gly | glycine |
| H | His | L-histidine |
| I | Ile | L-isoleucine |
| L | Leu | L-leucine |
| K | Lys | L-lysine |
| M | Met | L-methionine |
| N | Asn | L-asparagine |
| P | Pro | L-proline |
| dP | dPro | D-proline |
| dPen | | D-penicillamine |
| Pmc | | 2,2,5,7,8-pentamethylchroman-6-sulphonyl |
| Q | Gln | L-glutamine |
| R | Arg | L-arginine |
| S | Ser | L-serine |
| T | Thr | L-threonine |
| Trt | | trityl |
| V | Val | L-valine |
| W | Trp | L-tryptophan |
| dW | dTrp | D-tryptophan |
| Y | Tyr | L-tyrosine |
| Boc | | tert-butoxycarbonyl |
| DCM | | methylene chloride |
| Dic | | N,N'-diisopropyl carbodiimide |
| DIPEA | | diisopropyl-ethylamine |
| EDT | | 1,2-ethanedithiol |
| Fmoc | | 9-fluorenymethoxy-carbonyl |
| HOBT | | 1-hydroxy-1H-benzotriazol |
| HBTU | | O-benzotriazole-N,N,N',N'-tetra methyluronium-hexafluorophosphate |
| DMF | | N,N-dimehtyl formamide |
| MCPBA | | m-chloroperoxy benzoic acid |
| NMM | | N-methylmorpholine |
| TFA | | trifluoroacetic acid |

Modifications and changes can be made in the structure of a peptide of the present invention and still obtain a molecule that inhibits the binding of $\alpha_4\beta_1$ integrin. For example, certain amino acids can be substituted for other amino acids in a sequence without appreciable loss of activity; likewise, D- or L-amino acid residues can be used. D-amino acid residues are indicated herein as dXaa, where Xaa is the three letter code for a particular residue. In fact, certain amino acids can be substituted or added which greatly enhance binding inhibition. Because it is the interactive capacity and nature of a peptide that defines that peptide's biological functional activity, certain amino acid sequence substitutions can be made in a peptide sequence and nevertheless obtain a peptide with like properties, particularly inhibition of α$_4$β$_1$ integrin binding. Exemplary such peptides are set forth hereinafter.

Peptides of the present invention can vary in length (number of amino acid residue sequences) from 4 to about 13 residues. A peptide contemplated by the present invention is linear. A peptide of the present invention, has a free N-terminal amine (H) group, acetyl (Ac) group or a polyethyleneglycol moiety of 400 to 12,000 Daltons average molecular weight linked through an amide bond to the N-terminal residue, and a C-terminal carboxylic acid (OH) or amide (NH$_2$) group.

A peptide of the present invention is modeled after the Leu-Asp-Val domain of the CSI peptide sequence. In one embodiment, a peptide of the present invention comprises the Trp-Leu-Asp-Val sequence (SEQ ID NO:1) per se. In other embodiments, a peptide comprises an analog of SEQ ID NO:1 containing a single amino acid residue substitution. Such an analog can have the amino acid residue sequence Trp-Xaa$_1$-Asp-Val (SEQ ID NO:2) or Trp-Leu-Asp-Xaa$_2$ (SEQ ID NO:3), where Xaa$_1$ and Xaa$_2$ are independently any L-α amino acid. In a preferred embodiment, Xaa$_1$ is Ala, Cys, Gly, His, Lys, Leu, Met, Asn, Pro, Thr, Trp or Tyr and Xaa$_2$ is Ala, Cys, Phe, Gly, His, Ile, Leu, Gln, Arg, Ser, Thr, Val, Trp or Tyr. More preferably, Xaa$_1$ is Leu, Lys or Met and Xaa$_2$ is Val, Tyr, Trp or Phe.

In another embodiment, a peptide of the present invention comprises the amino acid residue sequence Glu-Trp-Leu-Asp-Val (SEQ ID NO:4) or an analog of SEQ ID NO:4 having a single amino acid substitution. In accordance with this embodiment, a peptide of the present invention comprises the amino acid residue sequence Xaa$_3$-Trp-Leu-Asp-Val (SEQ ID NO:5), Glu-Trp-Xaa$_1$-Asp-Val (SEQ ID NO:6) or Glu-Trp-Leu-Asp-Xaa$_2$ (SEQ ID NO:7), where Xaa$_1$ and Xaa$_2$ can be any L-α-amino acid and Xaa$_3$ can be any D- or L-α-amino acid. Preferred embodiments of Xaa$_1$ and Xaa$_2$ are the same as set forth above. Preferably, Xaa$_3$ is Glu, Asn, Pro, Gln, Ser, Thr, Tyr or Val.

In a particular embodiment, the Val residue of SEQ ID NOs:4–7 can be removed and still obtain a peptide of the present invention that inhibits α$_4$β$_1$ binding.

Any of the above sequences can be extended in the N- or C-terminal or both directions by the addition of from 1 to 5 D- or L-α-amino acid residues.

Exemplary and preferred peptides of the present invention are Gly-Pro-Glu-Trp-Leu-Asp-Val-Pro-Ser-Thr-amide (SEQ ID NO:8); Gly-Pro-Glu-Trp-Leu-Asp-Val-Pro-amide (SEQ ID NO:9); Asp-Pro-Glu-Trp-Leu-Asp-Val-Pro-Ser-Thr-amide (SEQ ID NO: 10); Ac-Trp-Leu-Asp-Val-amide (SEQ ID NO:11); Gly-Pro-Asn-Trp-Leu-Asp-Val-Pro-Ser-Thr-amide (SEQ ID NO:12); Glu-Trp-Leu-Asp-Val-amide (SEQ ID NO:13); Glu-Trp-Leu-Asp-Val-acid (SEQ ID NO: 14); Glu-Phe-Leu-Asp-Val-Pro-Glu-Phe-Leu-Asp-Val (SEQ ID NO: 15); Glu-Ile-Leu-Asp-Val-amide (SEQ ID NO: 16); <Glu-Trp-Leu-Asp-Val-amide (SEQ ID NO:17); Tyr-Pro-Glu-Trp-Leu-Asp-Val-Pro-amide (SEQ ID NO:18); Ile-Asp-Glu-Trp-Leu-Asp-Val-Pro-amide (SEQ ID NO:19); Pro-Glu-Trp-Leu-Asp-Val-Pro-amide (SEQ ID NO:20); Glu-Trp-Leu-Asp-Val-Pro-amide (SEQ ID NO:21); Gly-Pro-Glu-Trp-Leu-Asp-Val-amide (SEQ ID NO:22); Ac-Phe-Leu-Asp-Val-amide (SEQ ID NO:23); Gly-Pro-Glu-Cys-Leu-Asp-Val-Pro-amide (SEQ ID NO:24); Phe-Leu-Asp-Val-amide (SEQ ID NO:25); Gly-Pro-Glu-Met-Leu-Asp-Val-Pro-amide (SEQ ID NO:26); Gly-Pro-Glu-Val-Leu-Asp-Val-Pro-amide (SEQ ID NO:27); Trp-Leu-Asp-Val-amide (SEQ ID NO:28); Gly-Pro-Glu-Ala-Leu-Asp-Val-Pro-amide (SEQ ID NO:29); Gly-Pro-Glu-Asp-Leu-Asp-Val-Pro-amide (SEQ ID NO:30); Gly-Pro-Glu-Gly-Leu-Asp-Val-Pro-amide (SEQ ID NO:31); Gly-Pro-Glu-Lys-Leu-Asp-Val-Pro-amide (SEQ ID NO:32); Gly-Pro-Glu-Asn-Leu-Asp-Val-Pro-amide (SEQ ID NO:33); Gly-Pro-Glu-Trp-Leu-His-Val-Pro-amide (SEQ ID NO:34); Gly-Pro-Glu-Trp-Leu-Lys-Val-Pro-amide (SEQ ID NO:35); Gly-Pro-Glu-Ser-Leu-Asp-Val-Pro-amide (SEQ ID NO:36); Gly-Pro-Glu-Trp-Leu-Met-Val-Pro-amide (SEQ ID NO:37); Gly-Pro-Glu-Trp-Leu-Cys-Val-Pro-amide (SEQ ID NO:38); Gly-Pro-Glu-Trp-Leu-Glu-Val-Pro-amide (SEQ ID NO:39); Gly-Pro-Glu-Phe-Leu-Asp-Val-Pro-amide (SEQ ID NO:40); Gly-Pro-Glu-Pro-Leu-Asp-Val-Pro-amide (SEQ ID NO:41); Gly-dPro-dGlu-Trp-Leu-Asp-Val-Pro-amide (SEQ ID NO:42); Gly-Pro-dGlu-Trp-Leu-Asp-Val-Pro-amide (SEQ ID NO:43); Gly-dPro-Glu-Trp-Leu-Asp-Val-Pro-amide (SEQ ID NO:44); Gly-Pro-Glu-Trp-Leu-Asp-amide (SEQ ID NO:45); Gly-Pro-Glu-His-Leu-Asp-Val-Pro-amide (SEQ ID NO: 46); Gly-Pro-Glu-Leu-Leu-Asp-Val-Pro-amide (SEQ ID NO:47); Gly-Pro-Glu-Gln-Leu-Asp-Val-Pro-amide (SEQ ID NO:48); Gly-Pro-Glu-Thr-Leu-Asp-Val-Pro-amide (SEQ ID NO:49); Gly-Pro-GluoTrp-Leu-Phe-Val-Pro-amide (SEQ ID NO:50); Ac-Gly-Pro-Glu-Trp-Leu-Asp-Val-Pro-Ser-Thr-amide (SEQ ID NO:51); Gly-Pro-Glu-Trp-Leu-Asp-Phe-Pro-amide (SEQ ID NO:52); Glu-Trp-Leu-Asp-Phe-amide (SEQ ID NO:53); Gly-Pro-Glu-Trp-Leu-Asp-Tyr-Pro-amide (SEQ ID NO:54); Gly-Pro-Ser-Trp-Leu-Asp-Val-Pro-amide (SEQ ID NO:55); Gly-Pro-Gly-Trp-Leu-Asp-Val-Pro-amide (SEQ ID NO:56); Gly-ProoGln-Trp-Leu-Asp-Val-Pro-amide (SEQ ID NO:57); Gly-Pro-Asn-Trp-Leu-Asp-Val-Pro-amide (SEQ ID NO:58); Gly-Glu-Pro-Trp-Leu-Asp-Leu-Pro-amide (SEQ ID NO:59); Gly-Pro-Ala-Trp-Leu-Asp-Val-Pro-amide (SEQ ID NO:60); Gly-Pro-Glu-Trp-Leu-Asp-Cys-Pro-amide (SEQ ID NO:61); Gly-Pro-Cys-Trp-Leu-Asp-Val-Pro-amide (SEQ ID NO:62); Gly-Pro-Pro-Trp-Leu-Asp-Val-Pro-amide (SEQ ID NO:63); Gly-Pro-Asp-Trp-Leu-Asp-Val-Pro-amide (SEQ ID NO:64); Gly-Pro-His-Trp-Leu-Asp-Val-Pro-amide (SEQ ID NO:65); Gly-Pro-Phe-Trp-Leu-Asp-Val-Pro-amide (SEQ ID NO:66); Gly-Pro-Thr-Trp-Leu-Asp-Val-Pro-amide (SEQ ID NO:67); Gly-Glu-Pro-Trp-Leu-Asp-Gly-Pro-amide (SEQ ID NO:68); Gly-Pro-Lys-Trp-Leu-Asp-Val-Pro-amide (SEQ ID NO:69); Gly-Glu-Pro-Trp-Leu-Asp-Ile-Pro-amide (SEQ ID NO:70); Gly-Pro-Glu-Trp-Leu-Asp-Trp-Pro-amide (SEQ ID NO:71); Glu-Trp-Leu-Asp-Cys-amide (SEQ ID NO:72); Gly-Pro-Val-Trp-Leu-Asp-Val-Pro-amide (SEQ ID NO:73); Gly-Glu-Pro-Trp-Leu-Asp-His-Pro-amide (SEQ ID NO:74); Glu-Trp-Leu-Asp-Tyr-amide (SEQ ID NO:75); Gly-Pro-Glu-Trp-Leu-Arg-Val-Pro-amide (SEQ ID NO:76); Gly-Pro-Met-Trp-Leu-Asp-Val-Pro-amide (SEQ ID NO:77); Gly-Pro-Ile-Trp-Leu-Asp-Val-Pro-amide (SEQ ID NO: 78); Gly-Pro-Glu-Trp-Leu-Asp-Ala-Pro-amide (SEQ ID NO:79); Glu-Trp-Leu-Asp-Cys-acid (SEQ ID NO:80); Gly-Pro-Trp-Trp-Leu-Asp-Val-Pro-amide (SEQ ID NO: 81); Gly-Pro-Tyr-Trp-Leu-Asp-Val-Pro-amide (SEQ ID NO:82); Gly-Pro-Glu-Trp-Lys-Asp-Val-Pro-amide (SEQ ID NO:83); Gly-Pro-Glu-Trp-Met-Lys-Val-Pro-amide (SEQ ID NO:84); Gly-Pro-Leu-Trp-Leu-Asp-Val-Pro-amide (SEQ ID NO:85); Gly-Glu-Pro-Trp-Leu-Asp-Gln-Pro-amide (SEQ ID NO:86); Gly-Glu-Pro-Trp-Leu-Asp-Asn-Pro-amide (SEQ ID NO:87); Glu-Trp-Leu-Asp-Trp-amide (SEQ ID NO:88); Gly-Pro-Arg-Trp-Leu-Asp-Val-Pro-amide (SEQ ID NO:89); Gly-Glu-Pro-Trp-Leu-Asp-Met-Pro-amide (SEQ ID NO:90); Gly-Glu-Trp-Pro-Leu-Asp-Pro-Pro-amide (SEQ ID NO:91 ); Gly-Pro-Glu-Trp-Leu-Pro-Val-Pro-amide (SEQ ID NO:92); Gly-Pro-Glu-Trp-Leu-Asp-Glu-Pro-amide (SEQ ID NO:93); Gly-Pro-Glu-Trp-Leu-Asp-Asp-Pro-amide (SEQ ID NO:94); Gly-Glu-Pro- Trp-Leu-Asp-Arg-Pro-amide (SEQ ID NO:95); Gly-Glu-Pro-Trp-Leu-Asp-Ser-Pro-amide (SEQ ID NO:96); Gly-Pro-Glu-Trp-Leu-Gln-Val-Pro-amide (SEQ ID NO:97); Gly-Glu-Pro-Trp-Leu-Asp-Lys-Pro-amide (SEQ ID NO:98); Gly-Pro-Glu-Glu-Leu-Asp-Val-Pro-Ser-Thr-amide (SEQ ID NO:99); Gly-Pro-Glu-Trp-Leu-Asp-Tyr-Pro-Asn-Thr-amide (SEQ ID NO:100); Gly-Pro-Glu-Ile-Leu-Asp-Val-Pro-Ser-Thr-amide (SEQ ID NO:101) and Gly-Pro-Glu-Arg-Leu-Asp-Val-Pro-Ser-Thr-amide (SEQ ID NO:102).

A peptide of the present invention can be made using standard peptide synthetic procedures well known in the art. Typically, peptides were made with Fmoc-amino acids. However, peptides can also be made using Boc protecting groups by methods well known to those skilled in the art. Side chain protecting groups of trifunction amino acids used in the synthetic procedure include Arginine (Pmc), Aspattic acid (tBu), Cysteine (Trt), Glutamic acid (tBu), Histidine (Boc), Lysine (Boc), Serine (tBu), Threonine (tBu), and Tyrosine (tBu). Other protecting groups are specifically described.

The preparation of the peptides in this invention by solid phase methodology is well known to those skilled in the art, and can be described as follows. Peptides were synthesized on an insoluble carrier such as p-benzyloxybenzyl alcohol resin for the synthesis of C-terminal carboxylic acid peptides (Wang resin, where normally the resin can be purchased with the first amino acid bound), and 4-(2',4'-dimethoxyphenyl-Fmoc-aminomethyl)phenoxy resin for C-terminal amide peptides (Rink resin). The peptides were prepared by solid phase synthesis using either HBTU or DIC chemistry procedures on a Protein Technologies Inc. Symphony peptide synthesizer.

The C-terminal amide peptides were prepared by coupling the C-terminal amino acid of the sequence to the Rink resin using the same general method as the other couplings. The C-terminal carboxylic acid peptide were prepared by purchasing Wang resin to which the C-terminal amino acid was bound as a carboxylic ester. The α-amino protecting group was removed by piperidine treatment, and the next Fmoc-amino acid coupled to the resin by simultaneous treatment of the resin with the Fmoc-amino acid, a coupling reagent such as DIC or HBTU, and if necessary HOBT. Such deprotection and couplings were repeated to afford each desired peptide. In all cases the Fmoc protecting group was removed by treatment with a 20% solution of piperidine in DMF. However, it is understood by those skilled in the art that the exact percentage of piperidine is not critical and should not be considered limiting in this invention. It is also understood by those skilled in the art that piperidine can be replaced by other bases, furthermore the coupling reagents and protocols used can be substituted with any of those known in the field of peptide synthesis (including the use of Boc chemistry based solid phase synthesis and also solution phase peptide synthesis), and those reagents specifically used in the examples provided should not be considered limiting for this invention. All unnatural amino acids, D-amino acids and other compounds were coupled by manual addition of the reagent, following the same procedure as for automated operation.

Peptides were cleaved from the resin with a TFA cocktail after the removal of the N-terminal Fmoc protecting group. The exact composition of the TFA cocktail was varied depending on the side chain protecting groups present, and is well known to those skilled in the art. The range of TFA was from 85 to 95%, and the remainder comprised of a mixture of scavengers selected from a combination of anisole, thioanisole, cresol, thiocresol, phenol, thiophenol, EDT, trimethylsilane and water. The time of the cleavage reaction required was sequence dependant, normally being from 1 to 3 hours. After cleavage the resin was removed by filtration and cold ether added to the solution to give a precipitate. The precipitate was collected and washed a few times with ether to remove residual TFA and scavengers. The precipitate was redissolved in aqueous solution for lyophilization to give the crude product.

Purification of the crude peptide was carried out by reverse-phase HPLC on a $C_{18}$-column preparative column (300 Å, 21.4 mm×25 cm, 5 μm spherical packing) at a flow rate of 10 ml/min. The selection of any other suitable reverse-phase packing known to one skilled in the art is equally acceptable. Products were detected by UV absorption at 214 nm. Two mobile phases were used in the HPLC system, solution A and B using a gradient elution. Solution A was comprised of 5% acetonitrile in deionized water containing 0.15% TFA, while solution B comprised 5% of deionized water in acetonitrile containing 0.1% TFA. A gradient of increasing percentage of solution B was used to elute the peptide from the solid support, however the gradient used was sequence dependent, and can be selected by someone skilled in the art of peptide purification. Other methods of purification are equally acceptable. The purity of the peptides was checked by $C_{18}$ analytical HPLC (300 Å, 4.6 mm×25 cm, 5 μm spherical packing) at a flow rate of 1 ml/min.

A detailed description of the synthesis of exemplary peptides is set forth hereinafter in the Examples.

II. Pharmaceutical Composition

In another aspect, the present invention provides a pharmaceutical composition comprising a peptide of the present invention and a physiologically tolerable diluent. The present invention includes one or more peptides as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, or the like.

The compositions can be administered to humans and animals either orally, rectally, parenterally (intravenous, by intramuscularly or subcutaneously), intracisternally, intravaginally, intraperitoneally, intranasally, locally (powders, ointments or drops), or as a buccal or nasal spray or aerosol.

The compositions can also be delivered through a catheter for local delivery at a target site, via an intracoronary stent (a tubular device composed of a fine wire mesh), or via a biodegradable polymer. The compositions may also be complexed to ligands, such as antibodies, for targeted delivery of the compositions.

The compositions are preferably administered by catheter, i.v. or subcutaneous injection, or intranasally via a spray or aerosol.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Besides such inert diluents, the composition can also include adjuvants, such as wetting agents, emulsifying and suspending agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tmgacanth, or mixtures of these substances, and the like.

Dosage forms for topical administration of a compound of this invention include ointments, powders, sprays and inhalants. The active component is admixed under sterile conditions with a physiologically acceptable carrier and any preservatives, buffers or propellants as may be required. Ophthalmic formulations, eye ointments, powders and solutions are also contemplated as being within the scope of this invention.

III. Process of Inhibiting the Binding of $\alpha_4\beta_1$ Integrin to VCAM-1

In another aspect, the present invention contemplates a process of inhibiting the binding of $\alpha_4\beta_1$ integrin to VCAM-1. A process of the present invention can be used in vitro or in vivo in a living organism. In accordance with a process of the present invention, a cell expressing $\alpha_4\beta_1$ integrin is exposed to a cell expressing VCAM-1 in the presence of an effective inhibiting amount of a peptide of the present invention.

In a preferred embodiment, a peptide used in a process of the present invention comprises the amino acid residue sequence of SEQ ID NOs:1 or 4 and analogs thereof as set forth above. Means for determining an effective inhibiting amount are well known in the art.

A cell expressing $\alpha 4f 1$ integrin can be a naturally occurring white blood cell, mast cell or other cell type that naturally expresses $\alpha_4\beta_1$ on the cell surface, or a cell transfected with an expression vector that contains a polynucleotide (e.g., genomic DNA or cDNA) that encodes $\alpha_4\beta_1$ integrin. In an especially preferred embodiment, $\alpha_4\beta_1$ integrin is present on the surface of a white blood cell such as a monocyte, a lymphocyte or a granulocyte (e.g., an eosinophil or a basophil).

A cell that expresses VCAM-1 can be a naturally occurring cell (e.g. an endothelial cell) or a cell transfected with an expression vector containing a polynucleotide that encodes VCAM-1. Methods for producing transfected cells that express VCAM-1 are well known in the art.

Where VCAM-1 exists on the surface of cell, the expression of that VCAM-1 is preferably induced by inflammatory cytokines such as tumor necrosis factor-$\alpha$, interleukin-4 and interleukin-1$\beta$.

Where the cells expressing $\alpha_4\beta_1$ integrin and VCAM-1 are in a living organism, a peptide is administered in an effective amount to the living organism. Preferably, the peptide is in a pharmaceutical composition of this invention. Administering is preferably accomplished via intravascular injection or intranasal administration.

A process of the present invention is especially useful in treating diseases associated with uncontrolled migration of white blood cells to damaged tissue. Such diseases include, but are not limited to, asthma, atherosclerosis, rheumatoid arthritis, allergy, multiple sclerosis, leukemia, and bmin cancer.

A process of inhibiting VCAM-1 and $\alpha_4\beta_1$ binding uses a peptide of the present invention as set forth hereinbefore. Preferred such peptides are the same as set forth above. More preferably, a peptide used in a process of the present invention has the amino acid residue sequence of SEQ ID NO:8–102. Even more preferably, peptides have the amino acid residue sequence of SEQ ID NO:8–14, 17–23, 25, 28, and 51.

The present invention also provides a process of selectively inhibiting the binding of $\alpha_4\beta_1$ integrin to a protein comprising exposing the integrin to the protein in the presence of an effective inhibiting amount of a cyclic peptide of the present invention. In a preferred embodiment, the $\alpha_4\beta_1$ integrin is expressed on the surface of a cell, either naturally occuring or a cell transformed to express $\alpha_4\beta_1$ integrin.

The protein to which the $\alpha_4\beta_1$ integrin binds can be expressed on a cell surface or part of the extracellular matrix. Especially preferred proteins are fibronectin or invasin. Preferred peptides for use in such a process are the same as set forth above.

The ability of peptides of the present invention to inhibit binding are described in detail hereinafter in the Examples. The Examples illustrate particular embodiments of the present invention and are not limiting of the specification and claims in any way.

EXAMPLES

Example 1

Synthesis of Glu-Trp-Leu-Asp-Val-OH (SEQ ID NO:14) The Fmoc-amino acids were dissolved in DMF, and the coupling reagent HBTU was dissolved in DMF containing 0.4M NMM. The Fmoc- Vat-Wang resin (25 nM) was swollen by treatment with DMF (1.25 ml) for 15–20 min, then deprotected by treatment with 20% piperidine in DMF (3×, 8 min each), and the resin was washed with DMF (6×). Fmoc-Asp(tBu) (150 nM) and DIC (150 nM) were added to the resin and mixed with $N_2$ agitation for 40 min. The resin was washed with DMF (3×), and this procedure was repeated for each amino acid until the N-terminal residue was coupled. The N-terminal Fmoc group was deprotected with piperidine (3×, 8 min each) and washed with DMF (6×), and then DCM (6×). The resin was dried with a nitrogen stream for 15 min.

Cleavage of the peptide was achieved by treatment with a TFA cocktail (1.5 ml, containing 4% of thioanisole, 4% of thiophenol and 4% of EDT) at room temperature for one hour. The solution was filtered through glass wool, the volume reduced to about 0.5 ml and about 10 ml of cold ether was added. The precipitate was collected by centrifugation, washed with ether (3×) and lyophilized to give a white powder (12.2 mg).

Purification was carried out by reverse phase HPLC as described above using a gradient of 5–50% B during 60 min, and the pure EWLDV-acid isolated as a white powder by lyophilization (4.5 mg, >98% pure by analytical HPLC).

Other C-terminal carboxylic acids were prepared by an analogous procedure to that described in Example 1.

Example 2

Synthesis of
Asp-Pro-Glu-Trp-Leu-Asp-Val-Pro-Ser-Thr-NH$_2$
(SEQ ID NO:10)

The Fmoc amino acids and an equimolar amount of HOBT were dissolved in DMF, and DIC in DCM was used as the coupling reagent. The Fmoc-Rink resin (25 nM) was swollen by treatment with DMF (1.25 ml) for 15–20 min, then deprotected by treatment with 20% piperidine in DMF (3×, 8 min each), and the resin was washed with DMF (6×). The first amide bond was formed using Fmoc-Thr and a 1 to 1.2 hours coupling time. The remaining steps were analogous to those described in Example 1.

The HPLC purification conditions were analogous to those described in Example 1. The title compound, Asp-Pro-Glu-Trp-Leu-Asp-Val-Pro-Ser-Thr-amide was purified by reverse phase HPLC and isolated as a white powder by lyophilization (10.9 mg, >99% pure by analytical HPLC).

Example 3

Synthesis of
Ac-Gly-Pro-Glu-Trp-Leu-Asp-Val-Pro-Ser-Thr-NH$_2$,
(SEQ ID NO:51)

This peptide was prepared in the same manner as described in Example 2. After deprotection of the N-terminal Fmoc group, DMF containing 20% of acetic anhydride (3 ml) was added to the resin and stirred for 0.5 hour at room temperature, and the peptide was subsequently cleaved with TFA cocktail (1.5 ml, containing 4% of thioansole, 4% of thiophenol and 4% of EDT) for 1 hour.

The purification was carried out by reverse phase HPLC as described above using a gradient of 5–70% B during 60 min, and the pure compound isolated as a white powder by lyophilization (9.1 mg, >999 pure by analytical HPLC).

Example 4

Binding Assays

Peptides were assayed for their ability to inhibit the binding of the integrin $\alpha_4\beta_1$ to VCAM. The specificity of the most potent peptides as inhibitors of $\alpha_4\beta_1$ was determined using a fibronectin binding assay. The assays are described below.

The VCAM-1 binding assays involved assessing the ability of cells that express $\alpha_4\beta_1$ to bind cells expressing VCAM (cell-cell assay) or to bind purified VCAM protein (cell-protein assay). The integrin-expressing cell types used in these assays included the human B-cell line, Ramos, and the human promyelocytic line, HL-60. The cell-cell assay was used to compare the relative potency of peptides at a single dose. The cell-protein assay was used to generate dose response curves and determine IC$_{50}$ values.

1. Cell-Cell Assay

A human VCAM cDNA was amplified by the polymerase chain reaction (PCR) from cDNA reverse transcribed from RNA isolated from human umbilical vein endothelial cells. The VCAM cDNA was ligated into a mammalian expression vector and electroporated into chinese hamster ovary (CHO) cells. Cells were grown in G418 selective media and clones expressing high levels of VCAM were selected by FACS analysis.

VCAM expressing CHO cells and nontransfected CHO cells were plated in 48 well cluster dishes at a density of 50,000 cells/well 24 hour prior to assay. The dishes were washed with binding buffer (DMEM, 1% BSA, 1.0 mM MnCl$_2$, 0.02% sodium azide, pH 7.4) immediately prior to assay. Ramos cells which had been metabolically labelled with $^{35}$S-methionine and cysteine were incubated with the CHO cells (4×10$^5$ Ramos cells/well) in the presence or absence of peptide for 1 hour at 4° C. with rocking. Unbound cells were removed by washing with binding buffer and the remaining bound cells were lysed with 50 mM Tris, pH 8.0, 150 mM NaCl, 1% SDS and transferred to scintillation vials for quantitation.

2. Cell-Protein Assay

An expression vector was designed such that a region of VCAM known to bind the integrin was-expressed as a fusion protein with mouse IgG. A cDNA containing the two N-terminal domains of human VCAM was generated by the polymerase chain reaction (PCR) from a full length VCAM cDNA. Similarly, a cDNA containing the hinge, CH2 and CH3 regions of mouse IgG$_{2A}$ was amplified by PCR from cDNA made from total RNA isolated from the hybridoma cell line 402C10. The VCAM cDNA was ligated to the mouse IgG cDNA and cloned into a mammalian expression vector. Transfection of the plasmid into COS cells resulted in the expression and secretion of the fusion protein into the surrounding cell culture media. The media was collected and active protein was purified by immunoprecipitation using Dynal magnetic polystyrene beads coated with goat anti-mouse IgG. Following immunoprecipitation, the beads bound Ramos cells that expressed the integrin $\alpha_4\beta_1$. Beads incubated with media from mock transfected COS cells did not bind these cell types and served as a negative control for the assay.

Ramos cells were fluorescently labeled with calcein AM (Molecular Probes) and resuspended in 1 ml of binding buffer (Hanks' balanced salt solution, pH 7.4, 1.0 mM CaCl$_2$, 1.0 mM MgCl$_2$ and 1.0 mM MnCl$_2$). The beads (10 µl, 4×10$^6$ beads/ml) were placed in wells of a 96-well microtiter dish with 10 µl of peptide at various concentrations. The beads were incubated with 10 µl of labeled cells (10$^7$ cells/ml) for 10 min at room temperature. Following immobilization of the beads onto the plastic with a magnet, unbound cells were removed by washing three times with binding buffer. The remaining bound cells were lysed in 50 mM Tris, pH 7.4, 5.0 mM EDTA, 1.0% NP-40 and quantitated by fluorimetry using a Millipore Cytofluor 2350 fluorimeter. Dose response curves were calculated and IC$_{50}$ values determined. Peptides having the amino acid residue sequences of SEQ ID NOs:8–102 were tested for their ability to inhibit the binding of $\alpha_4\beta_1$ integrin to VCAM-1.

In a further study, amino acid residues in SEQ ID NO:9 were individually scanned with 20 natural amino acids and tested for inhibitory activity. The results are summarized below in Table 1 (numbers refer to relative quantity of adhered cells in relationship to peptide SEQ ID NO:9).

TABLE 1

| | SEQ ID NO:9 GPEWLDVP | | | | |
|---|---|---|---|---|---|
| Substitution: | E | W | L | D | V |
| A | 1.47 | 1.64 | 1.90 | 2.42 | 1.88 |
| C | 1.49 | 1.45 | 1.69 | 1.78 | 1.46 |
| D | 1.54 | 1.62 | 2.17 | 1.00 | 2.39 |
| E | 1.00 | 1.66 | 2.07 | 1.77 | 2.33 |

TABLE 1-continued

SEQ ID NO:9 GPEWLDVP

| Substitution: | E | W | L | D | V |
|---|---|---|---|---|---|
| F | 1.64 | 0.83 | 2.33 | 1.94 | 1.13 |
| G | 1.33 | 1.65 | 1.89 | 1.84 | 1.67 |
| H | 1.23 | 1.68 | 1.64 | 1.74 | 1.77 |
| I | 1.44 | 1.51 | 2.26 | 2.55 | 1.81 |
| K | 1.34 | 1.65 | 1.12 | 1.74 | 2.68 |
| L | 1.62 | 1.74 | 1.00 | 2.01 | 1.54 |
| M | 1.42 | 1.54 | 1.14 | 1.76 | 2.46 |
| N | 0.94 | 1.70 | 1.59 | 2.38 | 2.31 |
| P | 0.98 | 1.12 | 1.77 | 2.19 | 2.45 |
| Q | 0.93 | 1.81 | 2.44 | 2.35 | 1.97 |
| R | 1.52 | 1.20 | 2.33 | 2.14 | 1.52 |
| S | 0.85 | 1.76 | 2.33 | 2.14 | 1.54 |
| T | 0.98 | 1.47 | 1.90 | 2.23 | 1.32 |
| V | 1.04 | 1.53 | 2.14 | 2.14 | 1.00 |
| W | 1.17 | 1.00 | 1.32 | 2.58 | 1.08 |
| Y | 0.96 | 1.83 | 1.89 | 1.28 | 0.80 |

Peptides were assayed at a concentration of SEQ ID NO:9 that resulted in approximately 50% inhibition of adhesion in the cell-cell based assay. In independent cell-protein based assays the $IC_{50}$ of SEQ ID NO:9 was found to be 30 μM. A value of >2.00 in Table 1 indicates little or no inhibition of VCAM-$\alpha_4\beta_1$ binding at the concentration tested.

Peptides having the amino acid residue sequence of SEQ ID NOs: 11, 13, 14, 20–23, 25, 28 and 45 were found to significantly inhibit the binding of $\alpha_4\beta_1$ to VCAM-1 at a peptide concentration of less than about 100/μM.

3. Fibronectin/$\alpha_4\beta_1$ Binding Assay

Human plasma fibronectin was coated onto wells of a 96 well assay plate. Wells coated with BSA were used as a control for the assay. Following washing with Tris buffered saline, pH 7.4 (TBS), the wells were blocked with TBS containing 1% BSA. Ramos and K562 cells that had been fluorescently labelled with calcein AM were washed and resuspended in binding buffer (Hanks' balanced salt solution, pH 7.4, 1.0 mM $CaCl_2$, 1.0 mM $MgCl_2$, 1.0 mM $MnCl_2$). Cells were mixed with peptide at various concentrations and placed in the wells. The plate was incubated at 37° C. for 45 min. Following washing, the remaining bound cells were lysed with 1% NP-40 and quantitated by fluorimetry using a Millipore Cytofluor 2350 fluorimeter. Dose response curves were calculated.

The foregoing Examples illustrate particular embodiments of the present invention. One of ordinary skill in the art will readily appreciate that changes, modification and alterations can be made in those embodiments without departing from true scope and spirit of the invention.

What is claimed is:

1. An isolated and purified peptide of from 4 to about 13 amino acid residues having (a) an N-terminal amine group, acetyl group or a polyethylene glycol moiety of from about 400 to about 12,000 Daltons average molecular weight linked through an amide bond to the N-terminal residue; and (b) a C-terminal carboxylic acid group or amide group; said peptide comprising the amino acid residue sequence of SEQ ID NO:1 or a single amino acid substituent analog thereof, wherein the analog has the amino acid residue sequence of SEQ ID NO:2 or 3.

2. A peptide of claim 1 that comprises the amino acid residue sequence of SEQ ID NO:4 or a single amino acid substituent thereof, wherein the analog has the amino acid residue sequence of SEQ ID NO:5, 6 or 7.

3. A pharmaceutical composition comprising a physiologically acceptable diluent and a peptide of claim 1.

4. A composition of claim 3 wherein the peptide has the amino acid residue sequence of SEQ ID NO:8–15, 17–100 or 102.

5. A process of selectively inhibiting the binding of $\alpha_4\beta_1$ integrin to VCAM-1 comprising exposing a cell that expresses $\alpha_4\beta_1$ integrin to a cell that expresses VCAM-1 in the presence of an effective inhibiting amount of a peptide of claim 1.

6. A process of claim 5 wherein the cell that expresses $\alpha_4\beta_1$ integrin is a white blood cell, a mast cell or a tumor cell.

7. A process of claim 5 wherein the cell that expresses VCAM-1 is an endothelial cell.

8. A process of selectively inhibiting the adhesion of a cell that expresses $\alpha_4\beta_1$ integrin to a vascular endothelial cell that expresses VCAM-1 comprising exposing the cell or endothelial cell to an effective inhibiting amount of a peptide of claim 1.

9. A process of claim 8 wherein the cell expressing $\alpha_4\beta_1$ is a white blood cell, a mast cell or a tumor cell.

10. A process of claim 8 wherein the cell expressing $\alpha_4\beta_1$ and the endothelial cell are located in a living organism.

11. A process of selectively inhibiting the binding of $\alpha_4\beta_1$ integrin to a protein comprising exposing the integrin to the protein in the presence of an effective inhibiting amount of a peptide of claim 1.

12. A process of claim 11 wherein the $\alpha_4\beta_1$ integrin is expressed on the surface of a cell.

13. A process of claim 11 wherein the protein is part of the extracellular matrix.

14. A process of claim 11 wherein the protein is fibronectin or invasin.

15. A peptide having the amino acid residue sequence of any of SEQ ID NO:8–15, 17–100 or 102.

* * * * *

SEQUENCE LISTING ( 1 ) GENERAL INFORMATION:

( i i i ) NUMBER OF SEQUENCES: 102

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Trp Leu Asp Val
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label=Xaa
            / note="Xaa is any L-amino acid."

( x i ) SEQUENCE DESCRIPTION: SEQ ID NO:2:

Trp Xaa Asp Val
    1

( 2 ) INFORMATION FOR SEQ ID NO:3:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 4
    ( D ) OTHER INFORMATION: /label=Xaa
        / note="Xaa is any L-amino acid."

( x i ) SEQUENCE DESCRIPTION: SEQ ID NO:3:

Trp Leu Asp Xaa
1

( 2 ) INFORMATION FOR SEQ ID NO:4:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:4:

Glu Trp Leu Asp Val
1                  5

( 2 ) INFORMATION FOR SEQ ID NO:5:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=Xaa
        / note="Xaa is any D- or L-amino acid."

( x i ) SEQUENCE DESCRIPTION: SEQ ID NO:5:

Xaa Trp Leu Asp Val
1                  5

( 2 ) INFORMATION FOR SEQ ID NO:6:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 3
    ( D ) OTHER INFORMATION: /label=Xaa
        / note="Xaa is any L-amino acid."

( x i ) SEQUENCE DESCRIPTION: SEQ ID NO:6:

Glu Trp Xaa Asp Val
1                  5

( 2 ) INFORMATION FOR SEQ ID NO:7:

( i ) SEQUENCE CHARACTERISTICS:

( A ) LENGTH: 5 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 5
( D ) OTHER INFORMATION: /label=Xaa
/ note="Xaa is any L-amino acid."

( x i ) SEQUENCE DESCRIPTION: SEQ ID NO:7:

Glu Trp Leu Asp Xaa
1               5

( 2 ) INFORMATION FOR SEQ ID NO:8:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 10
( D ) OTHER INFORMATION: /label=Xaa
/ note="Xaa=Thr-NH2."

( x i ) SEQUENCE DESCRIPTION: SEQ ID NO:8:

Gly Pro Glu Trp Leu Asp Val Pro Ser Xaa
1               5                   10

( 2 ) INFORMATION FOR SEQ ID NO:9:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 8
( D ) OTHER INFORMATION: /label=Xaa
/ note="Xaa=Pro-NH2."

( x i ) SEQUENCE DESCRIPTION: SEQ ID NO:9:

Gly Pro Glu Trp Leu Asp Val Xaa
1               5

( 2 ) INFORMATION FOR SEQ ID NO:10:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 10
( D ) OTHER INFORMATION: /label=Xaa
/ note="Xaa=Thr-NH2."

( x i ) SEQUENCE DESCRIPTION: SEQ ID NO:10:

Asp Pro Glu Trp Leu Asp Val Pro Ser Xaa
1               5                   10

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa
            / note="Xaa=Ac-Trp."

( i x ) FEATURE:
        ( A ) NAME/KEY: Modified-site
        ( B ) LOCATION: 4
        ( D ) OTHER INFORMATION: /label=Xaa
            / note="Xaa=Val-NH2."

( x i ) SEQUENCE DESCRIPTION: SEQ ID NO:11:

Xaa  Leu  Asp  Xaa
  1

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 10
        ( D ) OTHER INFORMATION: /label=Xaa
            / note="Xaa=Thr-NH2."

( x i ) SEQUENCE DESCRIPTION: SEQ ID NO:12:

Gly  Pro  Asn  Trp  Leu  Asp  Val  Pro  Ser  Xaa
  1                  5                              10

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /label=Xaa
            / note="Xaa=Val-NH2."

( x i ) SEQUENCE DESCRIPTION: SEQ ID NO:13:

Glu  Trp  Leu  Asp  Xaa
  1                  5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:

(A) NAME/KEY: Modified-site
            (B) LOCATION: 5
            (D) OTHER INFORMATION: /label=Xaa
                / note="Xaa=Val-COOH."

(xi) SEQUENCE DESCRIPTION: SEQ ID NO:14:

Glu  Trp  Leu  Asp  Xaa
    1                   5

(2) INFORMATION FOR SEQ ID NO:15:

(i) SEQUENCE CHARACTERISTICS:
            (A) LENGTH: 11 amino acids
            (B) TYPE: amino acid
            (D) TOPOLOGY: linear (ii) MOLECULE TYPE: peptide (xi) SEQUENCE DESCRIPTION: SEQ ID NO:15:

Glu  Phe  Leu  Asp  Val  Pro  Glu  Phe  Leu  Asp  Val
    1                   5                        10

(2) INFORMATION FOR SEQ ID NO:16:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 5
            (D) OTHER INFORMATION: /label=Xaa
                / note="Xaa=Val-NH2."

(xi) SEQUENCE DESCRIPTION: SEQ ID NO:16:

Glu  Ile  Leu  Asp  Xaa
    1                   5

(2) INFORMATION FOR SEQ ID NO:17:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label=Xaa
                / note="Xaa=xGlu (pyroglutamic acid)."

(ix) FEATURE:
            (A) NAME/KEY: Modified-site
            (B) LOCATION: 5
            (D) OTHER INFORMATION: /label=Xaa
                / note="Xaa=Val-NH2."

(xi) SEQUENCE DESCRIPTION: SEQ ID NO:17:

Xaa  Trp  Leu  Asp  Xaa
    1                   5

(2) INFORMATION FOR SEQ ID NO:18:

(i) SEQUENCE CHARACTERISTICS:
            (A) LENGTH: 8 amino acids
            (B) TYPE: amino acid
            (D) TOPOLOGY: linear ( i i ) MOLECULE TYPE: peptide ( i x ) FEATURE:
    ( A ) NAME/KEY: Modified-site
    ( B ) LOCATION: 8
    ( D ) OTHER INFORMATION: /label=Xaa
        / note="Xaa=Pro-NH2."

( x i ) SEQUENCE DESCRIPTION: SEQ ID NO:18:

```
Tyr Pro Glu Trp Leu Asp Val Xaa
1               5
```

( 2 ) INFORMATION FOR SEQ ID NO:19:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:19:

```
Ile Asp Glu Trp Leu Asp Val Xaa
1               5
```

( 2 ) INFORMATION FOR SEQ ID NO:20:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 7
        ( D ) OTHER INFORMATION: /label=Xaa
            / note="Xaa=Pro-NH2."

( x i ) SEQUENCE DESCRIPTION: SEQ ID NO:20:

```
Pro Glu Trp Leu Asp Val Xaa
1               5
```

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /label=Xaa
            / note="Xaa=Pro-NH2."

( x i ) SEQUENCE DESCRIPTION: SEQ ID NO:21:

```
Glu Trp Leu Asp Val Xaa
1               5
```

( 2 ) INFORMATION FOR SEQ ID NO:22:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 7
    ( D ) OTHER INFORMATION: /label=Xaa
        / note="Xaa=Val-NH2."

( x i ) SEQUENCE DESCRIPTION: SEQ ID NO:22:

Gly  Pro  Glu  Trp  Leu  Asp  Xaa
1                           5

( 2 ) INFORMATION FOR SEQ ID NO:23:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa
            / note="Xaa=Ac-Phe."

( i x ) FEATURE:
        ( A ) NAME/KEY: Modified-site
        ( B ) LOCATION: 4
        ( D ) OTHER INFORMATION: /label=Xaa
            / note="Xaa=Val-NH2."

( x i ) SEQUENCE DESCRIPTION: SEQ ID NO:23:

Xaa  Leu  Asp  Xaa
1

( 2 ) INFORMATION FOR SEQ ID NO:24:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:24:

Gly  Pro  Glu  Cys  Leu  Asp  Val  Xaa
1                           5

( 2 ) INFORMATION FOR SEQ ID NO:25:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /label=Xaa / note="Xaa=Val-NH2."

( x i ) SEQUENCE DESCRIPTION: SEQ ID NO:25:

Phe Leu Asp Xaa
1

( 2 ) INFORMATION FOR SEQ ID NO:26:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 8
( D ) OTHER INFORMATION: /label=Xaa
/ note="Xaa=Pro-NH2."

( x i ) SEQUENCE DESCRIPTION: SEQ ID NO:26:

Gly Pro Glu Met Leu Asp Val Xaa
1               5

( 2 ) INFORMATION FOR SEQ ID NO:27:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 8
( D ) OTHER INFORMATION: /label=Xaa
/ note="Xaa=Pro-NH2."

( x i ) SEQUENCE DESCRIPTION: SEQ ID NO:27:

Gly Pro Glu Val Leu Asp Val Xaa
1               5

( 2 ) INFORMATION FOR SEQ ID NO:28:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 4
( D ) OTHER INFORMATION: /label=Xaa
/ note="Xaa=Val-NH2."

( x i ) SEQUENCE DESCRIPTION: SEQ ID NO:28:

Trp Leu Asp Xaa
1

( 2 ) INFORMATION FOR SEQ ID NO:29:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( i x ) FEATURE:
    ( A ) NAME/KEY: Modified-site
    ( B ) LOCATION: 8
    ( D ) OTHER INFORMATION: /label=Xaa
        / note="Xaa=Pro-NH2."

( x i ) SEQUENCE DESCRIPTION: SEQ ID NO:29:

Gly Pro Glu Ala Leu Asp Val Xaa
1               5

( 2 ) INFORMATION FOR SEQ ID NO:30:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:30:

Gly Pro Glu Asp Leu Asp Val Xaa
1               5

( 2 ) INFORMATION FOR SEQ ID NO:31:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:31:

Gly Pro Glu Gly Leu Asp Val Xaa
1               5

( 2 ) INFORMATION FOR SEQ ID NO:32:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:32:

Gly Pro Glu Lys Leu Asp Val Xaa
1               5

( 2 ) INFORMATION FOR SEQ ID NO:33:

( i ) SEQUENCE CHARACTERISTICS:
        ( A ) LENGTH: 8 amino acids
        ( B ) TYPE: amino acid ( D ) TOPOLOGY: linear ( i i ) MOLECULE TYPE: peptide ( i x ) FEATURE:
            ( A ) NAME/KEY: Modified-site
            ( B ) LOCATION: 8
            ( D ) OTHER INFORMATION: /label=Xaa
                    / note="Xaa=Pro-NH2."

( x i ) SEQUENCE DESCRIPTION: SEQ ID NO:33:

Gly   Pro   Glu   Asn   Leu   Asp   Val   Xaa
    1                       5

( 2 ) INFORMATION FOR SEQ ID NO:34:

( i ) SEQUENCE CHARACTERISTICS:
            ( A ) LENGTH: 8 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 8
            ( D ) OTHER INFORMATION: /label=Xaa
                    / note="Xaa=Pro-NH2."

( x i ) SEQUENCE DESCRIPTION: SEQ ID NO:34:

Gly   Pro   Glu   Trp   Leu   His   Val   Xaa
    1                       5

( 2 ) INFORMATION FOR SEQ ID NO:35:

( i ) SEQUENCE CHARACTERISTICS:
            ( A ) LENGTH: 8 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 8
            ( D ) OTHER INFORMATION: /label=Xaa
                    / note="Xaa=Pro-NH2."

( x i ) SEQUENCE DESCRIPTION: SEQ ID NO:35:

Gly   Pro   Glu   Trp   Leu   Lys   Val   Xaa
    1                       5

( 2 ) INFORMATION FOR SEQ ID NO:36:

( i ) SEQUENCE CHARACTERISTICS:
            ( A ) LENGTH: 8 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 8
            ( D ) OTHER INFORMATION: /label=Xaa
                    / note="Xaa=Pro-NH2."

( x i ) SEQUENCE DESCRIPTION: SEQ ID NO:36:

Gly   Pro   Glu   Ser   Leu   Asp   Val   Xaa
    1                       5

( 2 ) INFORMATION FOR SEQ ID NO:37:

( i ) SEQUENCE CHARACTERISTICS:
            ( A ) LENGTH: 8 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 8
            ( D ) OTHER INFORMATION: /label=Xaa
                    / note="Xaa=Pro-NH2."

( x i ) SEQUENCE DESCRIPTION: SEQ ID NO:37:

Gly  Pro  Glu  Trp  Leu  Met  Val  Xaa
    1                      5

( 2 ) INFORMATION FOR SEQ ID NO:38:

( i ) SEQUENCE CHARACTERISTICS:
            ( A ) LENGTH: 8 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 8
            ( D ) OTHER INFORMATION: /label=Xaa
                    / note="Xaa=Pro-NH2."

( x i ) SEQUENCE DESCRIPTION: SEQ ID NO:38:

Gly  Pro  Glu  Trp  Leu  Cys  Val  Xaa
    1                      5

( 2 ) INFORMATION FOR SEQ ID NO:39:

( i ) SEQUENCE CHARACTERISTICS:
            ( A ) LENGTH: 8 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 8
            ( D ) OTHER INFORMATION: /label=Xaa
                    / note="Xaa=Pro-NH2."

( x i ) SEQUENCE DESCRIPTION: SEQ ID NO:39:

Gly  Pro  Glu  Trp  Leu  Glu  Val  Xaa
    1                      5

( 2 ) INFORMATION FOR SEQ ID NO:40:

( i ) SEQUENCE CHARACTERISTICS:
            ( A ) LENGTH: 8 amino acids
            ( B ) TYPE: amino acid
            ( D ) TOPOLOGY: linear ( i i ) MOLECULE TYPE: peptide ( i x ) FEATURE:
            ( A ) NAME/KEY: Modified-site
            ( B ) LOCATION: 8
            ( D ) OTHER INFORMATION: /label=Xaa
                    / note="Xaa=Pro-NH2."

( x i ) SEQUENCE DESCRIPTION: SEQ ID NO:40:

Gly  Pro  Glu  Phe  Leu  Asp  Val  Xaa 1          5

(2) INFORMATION FOR SEQ ID NO:41:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /label=Xaa
            / note="Xaa=Pro-NH2."

(xi) SEQUENCE DESCRIPTION: SEQ ID NO:41:

Gly  Pro  Glu  Pro  Leu  Asp  Val  Xaa
    1                   5

(2) INFORMATION FOR SEQ ID NO:42:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /label=Xaa
            / note="Xaa=d-Pro."

(ix) FEATURE:
        (A) NAME/KEY: Modified-site
        (B) LOCATION: 3
        (D) OTHER INFORMATION: /label=Xaa
            / note="Xaa=d-Glu."

(ix) FEATURE:
        (A) NAME/KEY: Modified-site
        (B) LOCATION: 8
        (D) OTHER INFORMATION: /label=Xaa
            / note="Xaa=Pro-NH2."

(xi) SEQUENCE DESCRIPTION: SEQ ID NO:42:

Gly  Xaa  Xaa  Trp  Leu  Asp  Val  Xaa
    1                   5

(2) INFORMATION FOR SEQ ID NO:43:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /label=Xaa
            / note="Xaa=d-Glu."

(ix) FEATURE:
        (A) NAME/KEY: Modified-site
        (B) LOCATION: 8
        (D) OTHER INFORMATION: /label=Xaa
            / note="Xaa=Pro-NH2."

(xi) SEQUENCE DESCRIPTION: SEQ ID NO:43:

```
Gly  Pro  Xaa  Trp  Leu  Asp  Val  Xaa
 1                 5
```

( 2 ) INFORMATION FOR SEQ ID NO:44:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label=Xaa
            / note="Xaa=d-Pro."

( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:44:

```
Gly  Xaa  Glu  Trp  Leu  Asp  Val  Xaa
 1                 5
```

( 2 ) INFORMATION FOR SEQ ID NO:45:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /label=Xaa
            / note="Xaa=Asp-NH2."

( x i ) SEQUENCE DESCRIPTION: SEQ ID NO:45:

```
Gly  Pro  Glu  Trp  Leu  Xaa
 1                 5
```

( 2 ) INFORMATION FOR SEQ ID NO:46:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:46:

```
Gly  Pro  Glu  His  Leu  Asp  Val  Xaa
 1                 5
```

( 2 ) INFORMATION FOR SEQ ID NO:47:

( i ) SEQUENCE CHARACTERISTICS:
        ( A ) LENGTH: 8 amino acids
        ( B ) TYPE: amino acid
        ( D ) TOPOLOGY: linear (ii) MOLECULE TYPE: peptide (ix) FEATURE:
  (A) NAME/KEY: Modified-site
  (B) LOCATION: 8
  (D) OTHER INFORMATION: /label=Xaa
    / note="Xaa=Pro-NH2."

(xi) SEQUENCE DESCRIPTION: SEQ ID NO:47:

Gly Pro Glu Leu Leu Asp Val Xaa
1       5

(2) INFORMATION FOR SEQ ID NO:48:

(i) SEQUENCE CHARACTERISTICS:
  (A) LENGTH: 8 amino acids
  (B) TYPE: amino acid
  (D) TOPOLOGY: linear (ii) MOLECULE TYPE: peptide (ix) FEATURE:
  (A) NAME/KEY: Modified-site
  (B) LOCATION: 8
  (D) OTHER INFORMATION: /label=Xaa
    / note="Xaa=Pro-NH2."

(xi) SEQUENCE DESCRIPTION: SEQ ID NO:48:

Gly Pro Glu Gln Leu Asp Val Xaa
1       5

(2) INFORMATION FOR SEQ ID NO:49:

(i) SEQUENCE CHARACTERISTICS:
  (A) LENGTH: 8 amino acids
  (B) TYPE: amino acid
  (D) TOPOLOGY: linear (ii) MOLECULE TYPE: peptide (ix) FEATURE:
  (A) NAME/KEY: Modified-site
  (B) LOCATION: 8
  (D) OTHER INFORMATION: /label=Xaa
    / note="Xaa=Pro-NH2."

(xi) SEQUENCE DESCRIPTION: SEQ ID NO:49:

Gly Pro Glu Thr Leu Asp Val Xaa
1       5

(2) INFORMATION FOR SEQ ID NO:50:

(i) SEQUENCE CHARACTERISTICS:
  (A) LENGTH: 8 amino acids
  (B) TYPE: amino acid
  (D) TOPOLOGY: linear (ii) MOLECULE TYPE: peptide (ix) FEATURE:
  (A) NAME/KEY: Modified-site
  (B) LOCATION: 8
  (D) OTHER INFORMATION: /label=Xaa
    / note="Xaa=Pro-NH2."

(xi) SEQUENCE DESCRIPTION: SEQ ID NO:50:

Gly Pro Glu Trp Leu Phe Val Xaa
1       5

(2) INFORMATION FOR SEQ ID NO:51:

(i) SEQUENCE CHARACTERISTICS:

(A) LENGTH: 11 amino acids
(B) TYPE: amino acid
(D) TOPOLOGY: linear (ii) MOLECULE TYPE: peptide (ix) FEATURE:
(A) NAME/KEY: Modified-site
(B) LOCATION: 11
(D) OTHER INFORMATION: /label=Xaa
/note="Xaa=Ile-NH2."

(xi) SEQUENCE DESCRIPTION: SEQ ID NO:51:

Glu Ser Pro Phe Phe Ser Trp Arg Thr Gln Xaa
1               5                   10

(2) INFORMATION FOR SEQ ID NO:52:

(i) SEQUENCE CHARACTERISTICS:
(A) LENGTH: 8 amino acids
(B) TYPE: amino acid
(D) TOPOLOGY: linear (ii) MOLECULE TYPE: peptide (ix) FEATURE:
(A) NAME/KEY: Modified-site
(B) LOCATION: 8
(D) OTHER INFORMATION: /label=Xaa
/note="Xaa=Pro-NH2."

(xi) SEQUENCE DESCRIPTION: SEQ ID NO:52:

Gly Pro Glu Trp Leu Asp Phe Xaa
1               5

(2) INFORMATION FOR SEQ ID NO:53:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 5
(D) OTHER INFORMATION: /label=Xaa
/note="Xaa=Phe-NH2."

(xi) SEQUENCE DESCRIPTION: SEQ ID NO:53:

Glu Trp Leu Asp Xaa
1               5

(2) INFORMATION FOR SEQ ID NO:54:

(i) SEQUENCE CHARACTERISTICS:
(A) LENGTH: 8 amino acids
(B) TYPE: amino acid
(D) TOPOLOGY: linear (ii) MOLECULE TYPE: peptide (ix) FEATURE:
(A) NAME/KEY: Modified-site
(B) LOCATION: 8
(D) OTHER INFORMATION: /label=Xaa
/note="Xaa=Pro-NH2."

(xi) SEQUENCE DESCRIPTION: SEQ ID NO:54:

Gly Pro Glu Trp Leu Asp Tyr Xaa
1               5

(2) INFORMATION FOR SEQ ID NO:55:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /label=Xaa
            / note="Xaa=Pro-NH2."

(xi) SEQUENCE DESCRIPTION: SEQ ID NO:55:

Gly  Pro  Ser  Trp  Leu  Asp  Val  Xaa
    1                       5

(2) INFORMATION FOR SEQ ID NO:56:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /label=Xaa
            / note="Xaa=Pro-NH2."

(xi) SEQUENCE DESCRIPTION: SEQ ID NO:56:

Gly  Pro  Gly  Trp  Leu  Asp  Val  Xaa
    1                       5

(2) INFORMATION FOR SEQ ID NO:57:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /label=Xaa
            / note="Xaa=Pro-NH2."

(xi) SEQUENCE DESCRIPTION: SEQ ID NO:57:

Gly  Pro  Gln  Trp  Leu  Asp  Val  Xaa
    1                       5

(2) INFORMATION FOR SEQ ID NO:58:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /label=Xaa
            / note="Xaa=Pro-NH2."

(xi) SEQUENCE DESCRIPTION: SEQ ID NO:58:

```
        Gly  Pro  Asn  Trp  Leu  Asp  Val  Xaa
        1                   5
```

( 2 ) INFORMATION FOR SEQ ID NO:59:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:59:

```
        Gly  Glu  Pro  Trp  Leu  Asp  Leu  Xaa
        1                   5
```

( 2 ) INFORMATION FOR SEQ ID NO:60:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:60:

```
        Gly  Pro  Ala  Trp  Leu  Asp  Val  Xaa
        1                   5
```

( 2 ) INFORMATION FOR SEQ ID NO:61:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:61:

```
        Gly  Pro  Glu  Trp  Leu  Asp  Cys  Xaa
        1                   5.
```

( 2 ) INFORMATION FOR SEQ ID NO:62:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8

(D) OTHER INFORMATION: /label=Xaa
/ note="Xaa=Pro-NH2."

(xi) SEQUENCE DESCRIPTION: SEQ ID NO:62:

Gly Pro Cys Trp Leu Asp Val Xaa
1               5

(2) INFORMATION FOR SEQ ID NO:63:

(i) SEQUENCE CHARACTERISTICS:
(A) LENGTH: 8 amino acids
(B) TYPE: amino acid
(D) TOPOLOGY: linear (ii) MOLECULE TYPE: peptide (ix) FEATURE:
(A) NAME/KEY: Modified-site
(B) LOCATION: 8
(D) OTHER INFORMATION: /label=Xaa
/ note="Xaa=Pro-NH2."

(xi) SEQUENCE DESCRIPTION: SEQ ID NO:63:

Gly Pro Pro Trp Leu Asp Val Xaa
1               5

(2) INFORMATION FOR SEQ ID NO:64:

(i) SEQUENCE CHARACTERISTICS:
(A) LENGTH: 8 amino acids
(B) TYPE: amino acid
(D) TOPOLOGY: linear (ii) MOLECULE TYPE: peptide (ix) FEATURE:
(A) NAME/KEY: Modified-site
(B) LOCATION: 8
(D) OTHER INFORMATION: /label=Xaa
/ note="Xaa=Pro-NH2."

(xi) SEQUENCE DESCRIPTION: SEQ ID NO:64:

Gly Pro Asp Trp Leu Asp Val Xaa
1               5

(2) INFORMATION FOR SEQ ID NO:65:

(i) SEQUENCE CHARACTERISTICS:
(A) LENGTH: 8 amino acids
(B) TYPE: amino acid
(D) TOPOLOGY: linear (ii) MOLECULE TYPE: peptide (ix) FEATURE:
(A) NAME/KEY: Modified-site
(B) LOCATION: 8
(D) OTHER INFORMATION: /label=Xaa
/ note="Xaa=Pro-NH2."

(xi) SEQUENCE DESCRIPTION: SEQ ID NO:65:

Gly Pro His Trp Leu Asp Val Xaa
1               5

(2) INFORMATION FOR SEQ ID NO:66:

(i) SEQUENCE CHARACTERISTICS:
(A) LENGTH: 8 amino acids
(B) TYPE: amino acid
(D) TOPOLOGY: linear (ii) MOLECULE TYPE: peptide (ix) FEATURE:
    (A) NAME/KEY: Modified-site
    (B) LOCATION: 8
    (D) OTHER INFORMATION: /label=Xaa
        /note="Xaa=Pro-NH2."

(xi) SEQUENCE DESCRIPTION: SEQ ID NO:66:

Gly Pro Phe Trp Leu Asp Val Xaa
 1               5

(2) INFORMATION FOR SEQ ID NO:67:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /label=Xaa
            /note="Xaa=Pro-NH2."

(xi) SEQUENCE DESCRIPTION: SEQ ID NO:67:

Gly Pro Thr Trp Leu Asp Val Xaa
 1               5

(2) INFORMATION FOR SEQ ID NO:68:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /label=Xaa
            /note="Xaa=Pro-NH2."

(xi) SEQUENCE DESCRIPTION: SEQ ID NO:68:

Gly Glu Pro Trp Leu Asp Gly Xaa
 1               5

(2) INFORMATION FOR SEQ ID NO:69:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /label=Xaa
            /note="Xaa=Pro-NH2."

(xi) SEQUENCE DESCRIPTION: SEQ ID NO:69:

Gly Pro Lys Trp Leu Asp Val Xaa
 1               5

(2) INFORMATION FOR SEQ ID NO:70:

(i) SEQUENCE CHARACTERISTICS:
        (A) LENGTH: 8 amino acids (B) TYPE: amino acid
(D) TOPOLOGY: linear (ii) MOLECULE TYPE: peptide (ix) FEATURE:
    (A) NAME/KEY: Modified-site
    (B) LOCATION: 8
    (D) OTHER INFORMATION: /label=Xaa
        /note="Xaa=Pro-NH2."

(xi) SEQUENCE DESCRIPTION: SEQ ID NO:70:

```
Gly Glu Pro Trp Leu Asp Ile Xaa
1                   5
```

(2) INFORMATION FOR SEQ ID NO:71:

(i) SEQUENCE CHARACTERISTICS:
    (A) LENGTH: 8 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 8
    (D) OTHER INFORMATION: /label=Xaa
        /note="Xaa=Pro-NH2."

(xi) SEQUENCE DESCRIPTION: SEQ ID NO:71:

```
Gly Pro Glu Trp Leu Asp Trp Xaa
1                   5
```

(2) INFORMATION FOR SEQ ID NO:72:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 5
    (D) OTHER INFORMATION: /label=Xaa
        /note="Xaa=Cys-NH2."

(xi) SEQUENCE DESCRIPTION: SEQ ID NO:72:

```
Glu Trp Leu Asp Xaa
1               5
```

(2) INFORMATION FOR SEQ ID NO:73:

(i) SEQUENCE CHARACTERISTICS:
    (A) LENGTH: 8 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 8
    (D) OTHER INFORMATION: /label=Xaa
        /note="Xaa=Pro-NH2."

(xi) SEQUENCE DESCRIPTION: SEQ ID NO:73:

```
Gly Pro Val Trp Leu Asp Val Xaa
1                   5
```

(2) INFORMATION FOR SEQ ID NO:74:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /label=Xaa
            / note="Xaa=Pro-NH2."

(xi) SEQUENCE DESCRIPTION: SEQ ID NO:74:

Gly Glu Pro Trp Leu Asp His Xaa
    1                 5

(2) INFORMATION FOR SEQ ID NO:75:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /label=Xaa
            / note="Xaa=Tyr-NH2."

(xi) SEQUENCE DESCRIPTION: SEQ ID NO:75:

Glu Trp Leu Asp Xaa
    1             5

(2) INFORMATION FOR SEQ ID NO:76:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /label=Xaa
            / note="Xaa=Pro-NH2."

(xi) SEQUENCE DESCRIPTION: SEQ ID NO:76:

Gly Pro Glu Trp Leu Arg Val Xaa
    1                 5

(2) INFORMATION FOR SEQ ID NO:77:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /label=Xaa
            / note="Xaa=Pro-NH2."

(xi) SEQUENCE DESCRIPTION: SEQ ID NO:77:

```
Gly  Pro  Met  Trp  Leu  Asp  Val  Xaa
1                   5
```

( 2 ) INFORMATION FOR SEQ ID NO:78:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:78:

```
Gly  Pro  Ile  Trp  Leu  Asp  Val  Xaa
1                   5
```

( 2 ) INFORMATION FOR SEQ ID NO:79:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:79:

```
Gly  Pro  Glu  Trp  Leu  Asp  Ala  Xaa
1                   5
```

( 2 ) INFORMATION FOR SEQ ID NO:80:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /label=Xaa
            / note="Xaa=Cys-COOH."

( x i ) SEQUENCE DESCRIPTION: SEQ ID NO:80:

```
Glu  Trp  Leu  Asp  Xaa
1                   5
```

( 2 ) INFORMATION FOR SEQ ID NO:81:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa / note="Xaa=Pro-NH2."

( x i ) SEQUENCE DESCRIPTION: SEQ ID NO:81:

Gly Pro Trp Trp Leu Asp Val Xaa
1                   5

( 2 ) INFORMATION FOR SEQ ID NO:82:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:82:

Gly Pro Tyr Trp Leu Asp Val Xaa
1                   5

( 2 ) INFORMATION FOR SEQ ID NO:83:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:83:

Gly Pro Glu Trp Lys Asp Val Xaa
1                   5

( 2 ) INFORMATION FOR SEQ ID NO:84:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( D ) OTHER INFORMATION: /label=Xaa
            / note="Xaa=Pro-NH2."

( x i ) SEQUENCE DESCRIPTION: SEQ ID NO:84:

Gly Pro Glu Trp Met Lys Val Xaa
1                   5

( 2 ) INFORMATION FOR SEQ ID NO:85:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 8
    ( D ) OTHER INFORMATION: /label=Xaa
        / note="Xaa=Pro-NH2."

( x i ) SEQUENCE DESCRIPTION: SEQ ID NO:85:

Gly Pro Leu Trp Leu Asp Val Xaa
1                   5

( 2 ) INFORMATION FOR SEQ ID NO:86:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 8
    ( D ) OTHER INFORMATION: /label=Xaa
        / note="Xaa=Pro-NH2."

( x i ) SEQUENCE DESCRIPTION: SEQ ID NO:86:

Gly Glu Pro Trp Leu Asp Gln Xaa
1                   5

( 2 ) INFORMATION FOR SEQ ID NO:87:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 8
    ( D ) OTHER INFORMATION: /label=Xaa
        / note="Xaa=Pro-NH2."

( x i ) SEQUENCE DESCRIPTION: SEQ ID NO:87:

Gly Glu Pro Trp Leu Asp Asn Xaa
1                   5

( 2 ) INFORMATION FOR SEQ ID NO:88:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 5
    ( D ) OTHER INFORMATION: /label=Xaa
        / note="Xaa=Trp-NH2."

( x i ) SEQUENCE DESCRIPTION: SEQ ID NO:88:

Glu Trp Leu Asp Xaa
1             5

( 2 ) INFORMATION FOR SEQ ID NO:89:

( i ) SEQUENCE CHARACTERISTICS:
    ( A ) LENGTH: 8 amino acids
    ( B ) TYPE: amino acid (D) TOPOLOGY: linear (i i) MOLECULE TYPE: peptide (i x) FEATURE:
    (A) NAME/KEY: Modified-site
    (B) LOCATION: 8
    (D) OTHER INFORMATION: /label=Xaa
        / note="Xaa=Pro-NH2."

(x i) SEQUENCE DESCRIPTION: SEQ ID NO:89:

```
Gly  Pro  Arg  Trp  Leu  Asp  Val  Xaa
1                   5
```

(2) INFORMATION FOR SEQ ID NO:90:

(i) SEQUENCE CHARACTERISTICS:
    (A) LENGTH: 8 amino acids
    (B) TYPE: amino acid
    (D) TOPOLOGY: linear (i i) MOLECULE TYPE: peptide (i x) FEATURE:
    (A) NAME/KEY: Modified-site
    (B) LOCATION: 8
    (D) OTHER INFORMATION: /label=Xaa
        / note="Xaa=Pro-NH2."

(x i) SEQUENCE DESCRIPTION: SEQ ID NO:90:

```
Gly  Glu  Pro  Trp  Leu  Asp  Met  Xaa
1                   5
```

(2) INFORMATION FOR SEQ ID NO:91:

(i) SEQUENCE CHARACTERISTICS:
    (A) LENGTH: 8 amino acids
    (B) TYPE: amino acid
    (D) TOPOLOGY: linear (i i) MOLECULE TYPE: peptide (i x) FEATURE:
    (A) NAME/KEY: Modified-site
    (B) LOCATION: 8
    (D) OTHER INFORMATION: /label=Xaa
        / note="Xaa=Pro-NH2."

(x i) SEQUENCE DESCRIPTION: SEQ ID NO:91:

```
Gly  Glu  Trp  Pro  Leu  Asp  Pro  Xaa
1                   5
```

(2) INFORMATION FOR SEQ ID NO:92:

(i) SEQUENCE CHARACTERISTICS:
    (A) LENGTH: 8 amino acids
    (B) TYPE: amino acid
    (D) TOPOLOGY: linear (i i) MOLECULE TYPE: peptide (i x) FEATURE:
    (A) NAME/KEY: Modified-site
    (B) LOCATION: 8
    (D) OTHER INFORMATION: /label=Xaa
        / note="Xaa=Pro-NH2."

(x i) SEQUENCE DESCRIPTION: SEQ ID NO:92:

```
Gly  Pro  Glu  Trp  Leu  Pro  Val  Xaa
1                   5
```

(2) INFORMATION FOR SEQ ID NO:93:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 8
    ( D ) OTHER INFORMATION: /label=Xaa
            / note="Xaa=Pro-NH2."

( x i ) SEQUENCE DESCRIPTION: SEQ ID NO:93:

Gly Pro Glu Trp Leu Asp Glu Xaa
1               5

( 2 ) INFORMATION FOR SEQ ID NO:94:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 8
    ( D ) OTHER INFORMATION: /label=Xaa
            / note="Xaa=Pro-NH2."

( x i ) SEQUENCE DESCRIPTION: SEQ ID NO:94:

Gly Pro Glu Trp Leu Asp Asp Xaa
1               5

( 2 ) INFORMATION FOR SEQ ID NO:95:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 8
    ( D ) OTHER INFORMATION: /label=Xaa
            / note="Xaa=Pro-NH2."

( x i ) SEQUENCE DESCRIPTION: SEQ ID NO:95:

Gly Glu Pro Trp Leu Asp Arg Xaa
1               5

( 2 ) INFORMATION FOR SEQ ID NO:96:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 8
    ( D ) OTHER INFORMATION: /label=Xaa
            / note="Xaa=Pro-NH2."

( x i ) SEQUENCE DESCRIPTION: SEQ ID NO:96:

Gly Glu Pro Trp Leu Asp Ser Xaa (2) INFORMATION FOR SEQ ID NO:97:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /label=Xaa
            / note="Xaa=Pro-NH2."

(xi) SEQUENCE DESCRIPTION: SEQ ID NO:97:

Gly Pro Glu Trp Leu Gln Val Xaa
    1                 5

(2) INFORMATION FOR SEQ ID NO:98:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /label=Xaa
            / note="Xaa=Pro-NH2."

(xi) SEQUENCE DESCRIPTION: SEQ ID NO:98:

Gly Glu Pro Trp Leu Asp Lys Xaa
    1                 5

(2) INFORMATION FOR SEQ ID NO:99:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 10
        (D) OTHER INFORMATION: /label=Xaa
            / note="Xaa=Thr-NH2."

(xi) SEQUENCE DESCRIPTION: SEQ ID NO:99:

Gly Pro Glu Glu Leu Asp Val Pro Ser Xaa
    1               5                      10

(2) INFORMATION FOR SEQ ID NO:100:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 10
        (D) OTHER INFORMATION: /label=Xaa
            / note="Xaa=Thr-NH2."

( x i ) SEQUENCE DESCRIPTION: SEQ ID NO:100:

Gly Pro Glu Trp Leu Asp Tyr Pro Asn Xaa
1               5                   10

( 2 ) INFORMATION FOR SEQ ID NO:101:

( i ) SEQUENCE CHARACTERISTICS:
         ( A ) LENGTH: 10 amino acids
         ( B ) TYPE: amino acid
         ( D ) TOPOLOGY: linear ( i i ) MOLECULE TYPE: peptide ( i x ) FEATURE:
         ( A ) NAME/KEY: Modified-site
         ( B ) LOCATION: 10
         ( D ) OTHER INFORMATION: /label=Xaa
              / note="Xaa=Thr-NH2."

( x i ) SEQUENCE DESCRIPTION: SEQ ID NO:101:

Gly Pro Glu Ile Leu Asp Val Pro Ser Xaa
1               5                   10

( 2 ) INFORMATION FOR SEQ ID NO:102:

( i ) SEQUENCE CHARACTERISTICS:
         ( A ) LENGTH: 10 amino acids
         ( B ) TYPE: amino acid
         ( D ) TOPOLOGY: linear ( i i ) MOLECULE TYPE: peptide ( i x ) FEATURE:
         ( A ) NAME/KEY: Modified-site
         ( B ) LOCATION: 10
         ( D ) OTHER INFORMATION: /label=Xaa
              / note="Xaa=Thr-NH2."

( x i ) SEQUENCE DESCRIPTION: SEQ ID NO:102:

Gly Pro Glu Arg Leu Asp Val Pro Ser Xaa
1               5                   10